(12) United States Patent
Tsuda

(10) Patent No.: US 8,212,564 B2
(45) Date of Patent: Jul. 3, 2012

(54) OPEN MAGNETIC RESONANCE IMAGING APPARATUS

(75) Inventor: Munetaka Tsuda, Tokyo (JP)

(73) Assignee: Hitachi Medical Corporation, Tokyo (JP)

(*) Notice: Subject to any disclaimer, the term of this patent is extended or adjusted under 35 U.S.C. 154(b) by 423 days.

(21) Appl. No.: 12/602,528

(22) PCT Filed: Jun. 11, 2008

(86) PCT No.: PCT/JP2008/060643
§ 371 (c)(1),
(2), (4) Date: Dec. 1, 2009

(87) PCT Pub. No.: WO2008/153036
PCT Pub. Date: Dec. 18, 2008

(65) Prior Publication Data
US 2010/0176811 A1    Jul. 15, 2010

(30) Foreign Application Priority Data
Jun. 14, 2007 (JP) ................. 2007-157309

(51) Int. Cl.
*G01V 3/00* (2006.01)
(52) U.S. Cl. .................... 324/318; 324/319
(58) Field of Classification Search .......... 324/300–322; 600/407–445
See application file for complete search history.

(56) References Cited

U.S. PATENT DOCUMENTS

| | | | |
|---|---|---|---|
| 5,760,584 A | 6/1998 | Frederick | |
| 6,411,093 B2* | 6/2002 | Schwilch et al. | 324/322 |
| 6,954,068 B1* | 10/2005 | Takamori et al. | 324/318 |
| 7,098,661 B2* | 8/2006 | Nistler et al. | 324/318 |
| 7,403,010 B1* | 7/2008 | Hertz | 324/318 |
| 7,884,609 B2* | 2/2011 | Soutome et al. | 324/322 |
| 2001/0010464 A1 | 8/2001 | Takamori et al. | |

FOREIGN PATENT DOCUMENTS

| | | |
|---|---|---|
| JP | 2-143509 | 6/1990 |
| JP | 10-192254 | 7/1998 |
| JP | 2001-198104 | 7/2001 |
| JP | 2002-200055 | 7/2002 |
| JP | 2003-144409 | 5/2003 |
| JP | 2004-16585 | 1/2004 |
| JP | 2005-65752 | 3/2005 |
| JP | 2005-185318 | 7/2005 |

* cited by examiner

*Primary Examiner* — Brij Shrivastav
(74) *Attorney, Agent, or Firm* — Cooper & Dunham LLP (57) ABSTRACT

In an MRI apparatus having an open structure, vibration caused by eddy current is reduced with keeping the magnetic field shielding capability of a high frequency shield disposed between a gradient magnetic field coil and a high frequency coil. The high frequency shield comprises two conductive sheets 501, 503 which are divided into plural parts at different positions, and a dielectric sheet 502 sandwiched therebetween. Accordingly, in the high frequency shield, the electric resistivity to high frequency magnetic field is lower than the electric resistivity to the switching frequency of gradient magnetic field, whereby the high frequency shield can act as a uniform conductor to the high frequency magnetic field, exercise the shielding capability of the high frequency magnetic field, reduce eddy current occurring due to passage of gradient magnetic field therethrough and suppress vibration.

15 Claims, 11 Drawing Sheets

(a) EDDY CURRENT WHEN HIGH FREQUENCY SHIELD IS NOT DIVIDED

EDDY CURRENT i (b) EDDY CURRENT WHEN HIGH FREQUENCY SHIELD IS DIVIDED INTO TWO PARTS

EDDY CURRENT i/2      EDDY CURRENT i/2

OPEN MAGNETIC RESONANCE IMAGING APPARATUS

TECHNICAL FIELD

This application is a 371 of PCT/JP2008/060643 filed Jun. 11, 2008.

The present invention relates to a magnetic resonance imaging apparatus (referred to as MRI apparatus), and particularly to an MRI apparatus designed so that an examination space is broad and open and also noise caused by an examination can be reduced.

BACKGROUND ART

An MRI apparatus in which an examinee is disposed in a uniform magnetic field space and executing a medical diagnosis on the basis of a nuclear magnetic resonance (hereinafter referred to as NMR) signal is used in a medical institution as in the case of examinations based on conventional CT apparatus and RI apparatus. Particularly, the examination using the MRI apparatus enables various examinations for imaging morphological information and functional information such as metabolism, etc. and has excellent lesion detecting capability.

The MRI apparatus contains a magnetostatic field generating device for forming a uniform magnetic field space, a high-frequency coil and a gradient magnetic field coil. The high frequency coil irradiates an examinee with a high-frequency magnetic field pulse to excite the examinee, and receives an NMR signal emitted from the examinee. The gradient magnetic field coil applies a gradient magnetic field pulse in a predetermined direction to the examinee so that the NMR signal is provided with position information.

The high frequency coil constitutes an LC circuit which is designed to electrically resonate at a resonance frequency co. The gradient magnetic field coil is constructed by winding a conductor in orthogonal three axial directions at high density. When the gradient magnetic field coil is disposed between the high frequency coil and the examinee, it disturbs transmission and reception of high-frequency magnetic field pulses. Therefore, the high frequency coil is normally disposed to be proximate to the examinee, and the gradient magnetic field coil is disposed at the outside of the high frequency coil. Even in such an arrangement, when the high frequency coil and the gradient magnetic field coil are close to each other, local inductive inductance and floating capacity occurs in the high-frequency magnetic field coil in the neighborhood of a position where the coil pattern of the high frequency coil is close to the coil pattern of the gradient magnetic field coil. Accordingly, the high frequency coil is not a uniform LC circuit, and thus there occurs a problem that the high frequency magnetic field generated by the high frequency coil is non-uniform.

In order to solve this problem, the construction that a magnetic shield (high frequency shield) of copper foil or the like is disposed between the high frequency coil and the gradient magnetic field coil is known (patent document 1). However, there occurs a problem that high frequency magnetic field emitted from the high frequency coil to the examinee is weakened by the magnetic coupling between the high frequency shield and the high frequency coil. In order to solve this problem, the patent document 1 discloses that the high frequency shield is attached to the bobbin of the gradient magnetic field coil to increase the interval between the high frequency shield and the high frequency coil and weak the magnetic coupling therebetween.

Furthermore, it has been known in the MRI apparatus that vibration occurs in the gradient magnetic field coil due to Lorentz force when it is operated, and thus it serves as a noise generating source (patent document 1, patent document 2). This noise problem occurs in both of a tunnel structure and an open structure. In order to reduce this noise problem, the patent document 1 discloses an MRI apparatus having a tunnel structure in which the gradient magnetic field coil is sealed in a low-pressure container. The patent document 2 discloses an MRI apparatus having an open structure in which the gradient magnetic field coil is surrounded by a shielding cover.

Patent document 1: JP-A-2001-1998104
Patent document 2: JP-A-2001-299719

DISCLOSURE OF THE INVENTION

Problem to be Solved by the Invention

As described above, when the magnetic field (high frequency shield) of copper foil or the like is disposed between the high frequency coil and the gradient magnetic field coil, the gradient magnetic field generated by the gradient magnetic field coil passes through the high frequency shield. Therefore, eddy current is induced in the high frequency shield by the magnetic flux of the gradient magnetic field. The magnitude of the eddy current is proportional to the total magnetic flux ($\Phi$) passing through the conductor and the variation speed, and it is represented by $d\Phi/dt$. Recently, a high speed imaging method which is represented by EPI (eco planar imaging) as a main imaging method of the MRI apparatus switches a strong gradient magnetic field pulse at a high speed, and thus the eddy current is increased.

The eddy current generated in the high frequency shield due to the gradient magnetic field generates a magnetic flux in the direction vertical to the main plane of the high frequency shield. In the MRI apparatus having the open structure, the direction of magnetostatic field generated by a flat plate-shaped magnet is vertical to the main plane, and thus the magnetostatic field direction is coincident with the direction of the magnetic flux generated by the eddy current. The electromagnetic force action thereof applies force to the high frequency shield. The direction of the force concerned is inverted in connection with the switching of the gradient magnetic field, and thus vibration occurs in the high frequency shield. Therefore, there occurs a problem that the high frequency shield serves as a new noise source.

This problem is inherent to the MRI apparatus having the open structure, and it does not occur in the MRI apparatus having the tunnel structure in which the magnetic flux direction of the eddy current is vertical to the direction of magnetostatic field.

In order to reduce the vibration of the high frequency shield, it is desired to reduce the eddy current of the high frequency shield. However, it is impossible to adopt the structure that the shielding capability of the high frequency magnetic field is lowered to reduce the eddy current.

The present invention has been implemented in view of the foregoing point, and has an object to reduce vibration caused by eddy current with keeping the magnetic field shielding capability of the high frequency shield disposed between the gradient magnetic field coil and the high frequency coil in the MRI apparatus having the open structure.

Means of Solving the Problem

In order to solve the above problem, according to the present invention, an MRI apparatus described below is provided. That is, the open type magnetic resonance imaging apparatus of this invention comprises a pair of magnetostatic field generators that are divisionally arranged at upper and lower sides of an imaging space in which an examinee is mounted; a pair of gradient magnetic field generators that are disposed at the imaging space sides of the pair of magnetostatic field generators; and a pair of high frequency generators that are disposed at the imaging space sides of the gradient magnetic field generators, wherein a high frequency shield is disposed between each gradient magnetic field generator and each high frequency generator to shield electromagnetic field generated by the high frequency generator. The high frequency shield has a structure of suppressing vibration occurring in the high frequency shield due to switching of gradient magnetic field generated by the gradient magnetic field generator.

As the structure of suppressing the vibration may be adopted a structure that the high frequency shields are fixed to support members fixed to the surfaces of the imaging space sides of the pair of magnetostatic field generators as the structure of suppressing the vibration. Accordingly, the rigidity of the high frequency shield can be enhanced, and the vibration of the high frequency shield can be suppressed. It is desired that the natural frequency of the support member is set to a frequency different from a switching frequency of the gradient magnetic field of the gradient magnetic field generator under the state that the high frequency shield is fixed to the support member. Accordingly, even when eddy current caused by gradient magnetic field occurs in the high frequency shield and the high frequency shield vibrates at the switching frequency of the gradient magnetic field, no resonance occurs in the support member, and thus occurrence of great vibration due to resonance can be prevented.

The high frequency shield can be designed so that the electric resistivity thereof to high frequency magnetic field generated by the high frequency generator is lower than the electric resistivity thereof to a switching frequency of gradient magnetic field generated by the gradient magnetic field generator. Accordingly, the high frequency shield can act as a uniform conductor to the high frequency magnetic field, exercise the shielding capability of high frequency magnetic field, reduce eddy current occurring due to passage of gradient magnetic field therethrough and suppress vibration.

For example, the high frequency shield may contain two conductive sheets and a dielectric sheet sandwiched therebetween, and the two conductive sheets may be respectively divided into plural parts at different positions. Accordingly, the high frequency shield may constitute an electrical circuit equivalent to serially connected capacitance elements by plural divided conductive sheets and a dielectric sheet sandwiched therebetween. In such an equivalent circuit, the electric resistivity to the high frequency magnetic field can be set to be lower than the electric resistivity to the switching frequency of the gradient magnetic field.

The dividing number of the foregoing two conductive sheets may be set to a value from not less than 10 to not more than 27. Accordingly, the eddy current can be reduced to ¹/₁₀ or less of the case where the conductive sheet is not divided, and the resistivity to the high frequency magnetic field of the high frequency generator can be suppressed to 5% or less of the impedance of the high frequency coil.

The support member of the foregoing high frequency shield may be configured to support the high frequency shield at a position which is spaced from the gradient magnetic field generator at a predetermined interval. Accordingly, the interval between the high frequency generator and the high frequency shield can be kept constant without being affected by the expansion and contraction of the gradient magnetic field, so that the high frequency magnetic field can be uniformly shielded.

The support member may be configured to cover the gradient magnetic field generator above the magnetostatic field generator. Accordingly, the support member can also serve as a shielding member for closing the space in which gradient magnetic field generator is disposed, and the noise of the gradient magnetic field generator can be reduced.

The magnetostatic field generator may has a recess portion on the surface thereof at the imaging space side. In this case, the gradient magnetic field generator may be disposed in the recess portion, and the support member shields an opening of the recess portion. Accordingly, the support member can also serve as the shielding member for setting, as a closed space, the space in which the gradient magnetic field generator is disposed, and the noise of the gradient magnetic field generator can be reduced.

EFFECT OF THE INVENTION

According to the present invention, in the MRI apparatus having the open structure, the vibration caused by the eddy current can be reduced with keeping the magnetic field shielding capability of the high frequency shield disposed between the gradient magnetic field coil and the high frequency coil, and the high frequency shield can be prevented from serving as a new noise source.

BRIEF DESCRIPTION OF THE DRAWINGS

FIG. 5(a) is a perspective view of a shield support member of the MRI apparatus, and (b) is a cross-sectional view thereof.

FIG. 6(a) is a top view of a high-frequency shield 111 of the MRI apparatus of FIG. 1, (b) is a cross-sectional view thereof, and (c) is an equivalent circuit diagram thereof.

FIG. 7(a) is a diagram showing eddy current when a non-divided circular conductive foil is used as a high frequency shield, and (b) is a diagram showing eddy current when a bisected circular conductive foil is used as the high frequency shield.

DESCRIPTION OF THE RELATED ART 101 superconductive magnet, 102 examinee, 103 upper cryostat, 104 lower cryostat, 105 joint pipe, 106 cryo-cooler, 108a, 108b gradient magnetic field coil, 109 gradient magnetic field power amplifier, 110 shield supporter, 111 high frequency shield, 112 high frequency coil, 113 high frequency power amplifier, 114 detection coil, 115 high frequency amplifying circuit, 116 computer, 117 display, 118 system signal bus line, 201 superconductive coil, 203 imaging space, 206 shielding plate, 207 vacuum container, 208 rubber cushion, 605 shield supporter

BEST MODES FOR CARRYING OUT THE INVENTION

Embodiments according to the present invention will be described hereunder with reference to the accompanying drawings. In all the drawings to describe the embodiments of the present invention, elements having the same functions are represented by the same reference numerals, and the repetitive description thereof is omitted.
(First Embodiment)

A superconductive open MRI apparatus according to a first embodiment will be described. In this embodiment, flat plate type gradient magnetic field coil and high frequency coil are secured to a superconductive magnet having an open structure, and a high frequency shield is disposed between the gradient magnetic field coil and the high frequency coil. In order to prevent vibration caused by eddy current from occurring in the high frequency shield and thus serve as a noise source in the above structure, this embodiment adopts the following constructions (1) to (3). (1) A high frequency shield structure that can reduce eddy current occurring in the high frequency shield with keeping the function of the high frequency shield is adopted. (2) The high frequency shield is supported by a support member having large rigidity to enhance the rigidity of the high frequency shield. (3) In order to prevent the high frequency shield from resonating due to switching of gradient magnetic field, the resonance frequencies of the high frequency shield and the support member are deviated from the operating frequency of the gradient magnetic field.

These constructions (1) to (3) provide a superconductive open MRI apparatus in which the environment of an examinee-mounted space is open and has little noise. The details of this embodiment will be described hereunder with reference to FIGS. 1 to 4.

Figure 1:
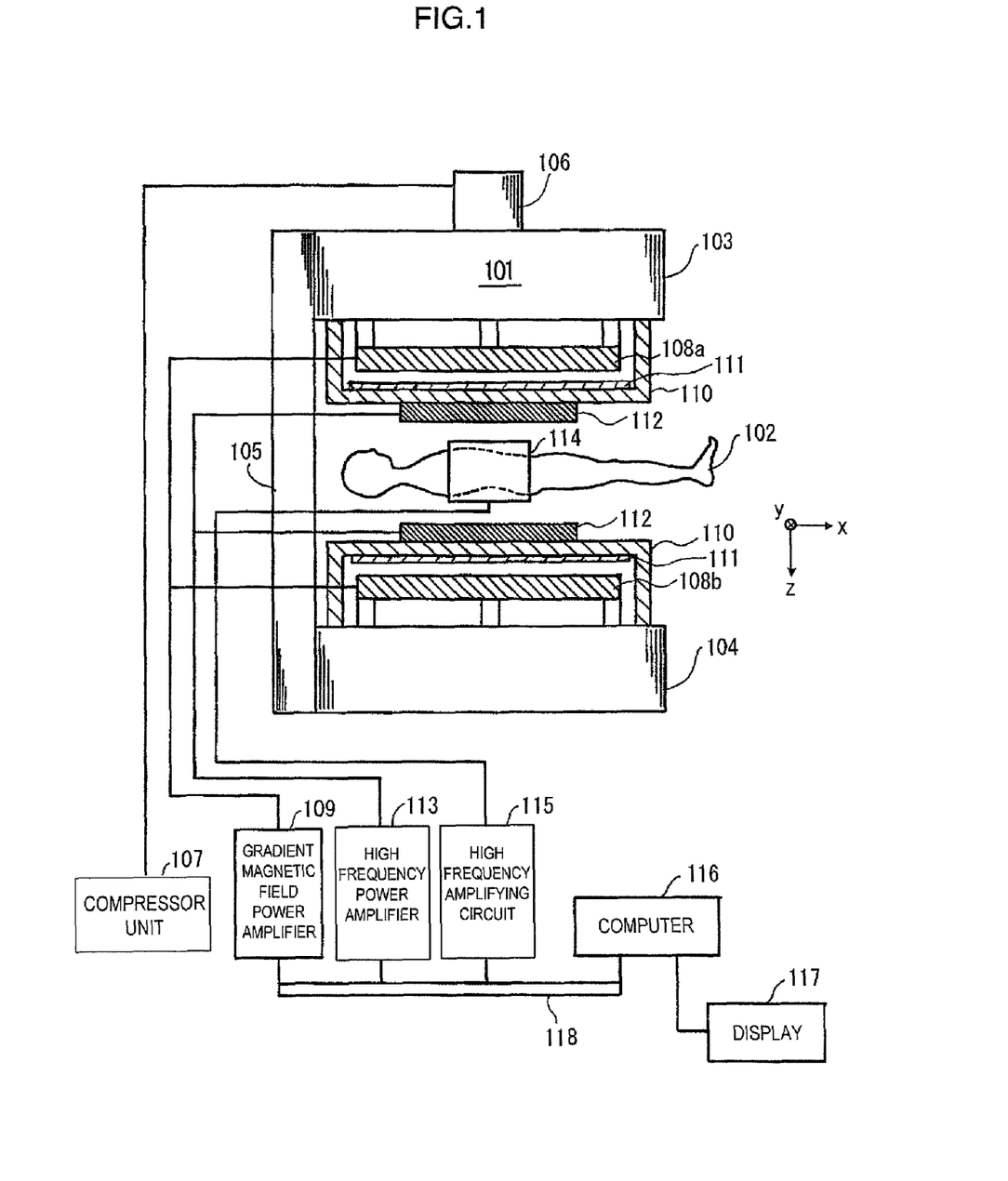
FIG. 1 is a block diagram showing the overall construction of a superconductive open MRI apparatus according to a first embodiment.
Figure 2:
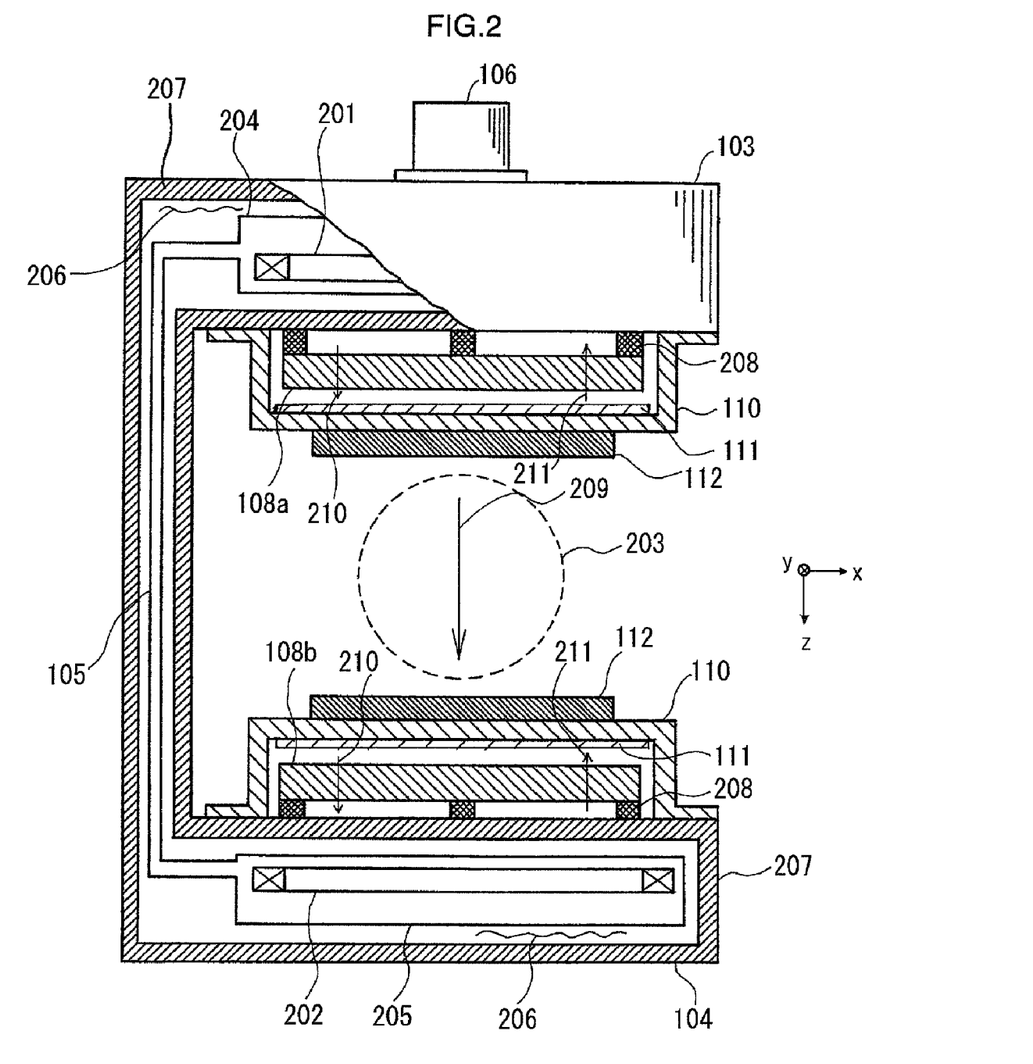
FIG. 2 is a cross-sectional view of a superconductive magnet of the MRI apparatus of FIG. 1.

First, the overall construction of the superconductive open MRI apparatus according to this embodiment will be described with reference to FIGS. 1 and 2. FIG. 1 is a diagram showing the overall construction of the superconductive open MRI apparatus using a superconductive magnet 101 having an open structure to which the present invention is applied. FIG. 2 is a cross-sectional view of the superconductive magnet 101 and a portion fixed to the superconductive magnet 101. As shown in FIGS. 1 and 2, the superconductive open MRI apparatus comprises the superconductive magnet 101 having the open structure, gradient magnetic field coils 108a, 108b, a high frequency coil 112, a high frequency shield 111, and a detection coil 114. A compressor unit 107, a gradient magnetic field power amplifier 109, a high frequency power amplifier 113 and a high frequency amplifying circuit 115 shown in FIG. 1 are connected to these elements. As shown in FIG. 1, the MRI apparatus is provided with a computer 116 and a display 117.

As shown in FIGS. 1 and 2, the superconductive magnet 101 having the open structure has an upper cryostat 103 and a lower cryostat 104 which are disposed so as to face each other through an imaging space 203 in which an examinee 102 is disposed. The main planes of the upper and lower cryostats 103 and 104 are in horizontal position. The upper cryostat 103 and the lower cryostat 104 are opposed to each other, and thus the imaging space 203 is greatly opened in the front-and-back direction and the right-and-left direction.

As shown in FIG. 2, the upper cryostat 103 contains an upper helium container 204 in which liquid helium is stocked, and a superconductive coil 201 disposed in the upper helium container 204. Likewise, the lower cryostat 104 contains a lower helium container 205 in which liquid helium is stocked and a superconductive coil 202 disposed in the lower helium container 205. The upper helium container 204 and the lower helium container 205 are joined to each other by a joint pipe 105 which also serves as a support pole. The outside of the upper and lower helium containers 204 and 205 and the outermost portion of the joint pipe 105 are covered by a vacuum container 207 having sufficient rigidity. For example, the vacuum container 207 may be formed of stainless steel at a thickness of 15 mm. A heat shield plate 206 (only a part thereof is shown) for preventing invasion of heat from the outside is disposed in the space between the vacuum container 207 and the upper and lower helium containers 204, 205 and in the space between the vacuum container 207 and the joint pipe 105. A superconductive lead wire for connecting the superconductive coils 201 and 202 and various kinds of sensor circuits (not shown in FIGS. 1 and 2) are disposed in the joint pipe 105.

The superconductive coils 201 and 202 generate magnetostatic field in a direction 209 from the upper cryostat 103 to the lower cryostat 104 in the imaging space 203. For example, magnetostatic field which has a magnetic field intensity of 1.2 tesla and is within uniformity degree of 3 ppm can be generated in the imaging space 203 of 40 cm in diameter. Each of the superconductive coils 201, 202 can be constructed by plural superconductive coils to increase the magnetic field intensity and improve the uniformity degree of magnetic field and a leakage magnetic field distribution.

A cryo-cooler 106 for re-condensing vaporized helium gas is secured to the upper cryostat 103 as shown in FIG. 1. The compressor unit 107 is connected to the cryo-cooler 106. The compressor unit 107 compresses helium gas under high pressure, and feeds the compressed helium gas to the cryo-cooler 106. The cryo-cooler 106 re-condenses helium gas in the upper cryostat 103. The re-condensed liquid helium is supplied from the upper cryostat 103 through the joint pipe 105 into the lower cryostat 104. As described above, the joint pipe 105 and the cryo-cooler 106 are provided, whereby the vaporized helium gas can be re-condensed and used as refrigerant although the superconductive magnet 101 has such an open structure that it is divided into the upper cryostat 103 and the lower cryostat 104. Accordingly, the superconductive magnet 101 can implement a hermetically sealed type cryostat as in the case of a superconductive magnet comprising only one cryostat in spite of the open structure.

The gradient magnetic field coils 108a and 108b are fixed through plural rubber cushions 208 to the faces at the imaging space 203 side of the upper cryostat 103 and the lower cryostat 104. The gradient magnetic field coils 108a and 108b are designed in a flat-plate structure so as not to obstruct the open structure of the superconductive magnet 101. Each of the gradient magnetic field coils 108a and 108b is constructed by laminating x, y, z coils, filling resin in the gaps thereof and hardening the resin so that the coils are firmly integrated with one another.

Figure 3:
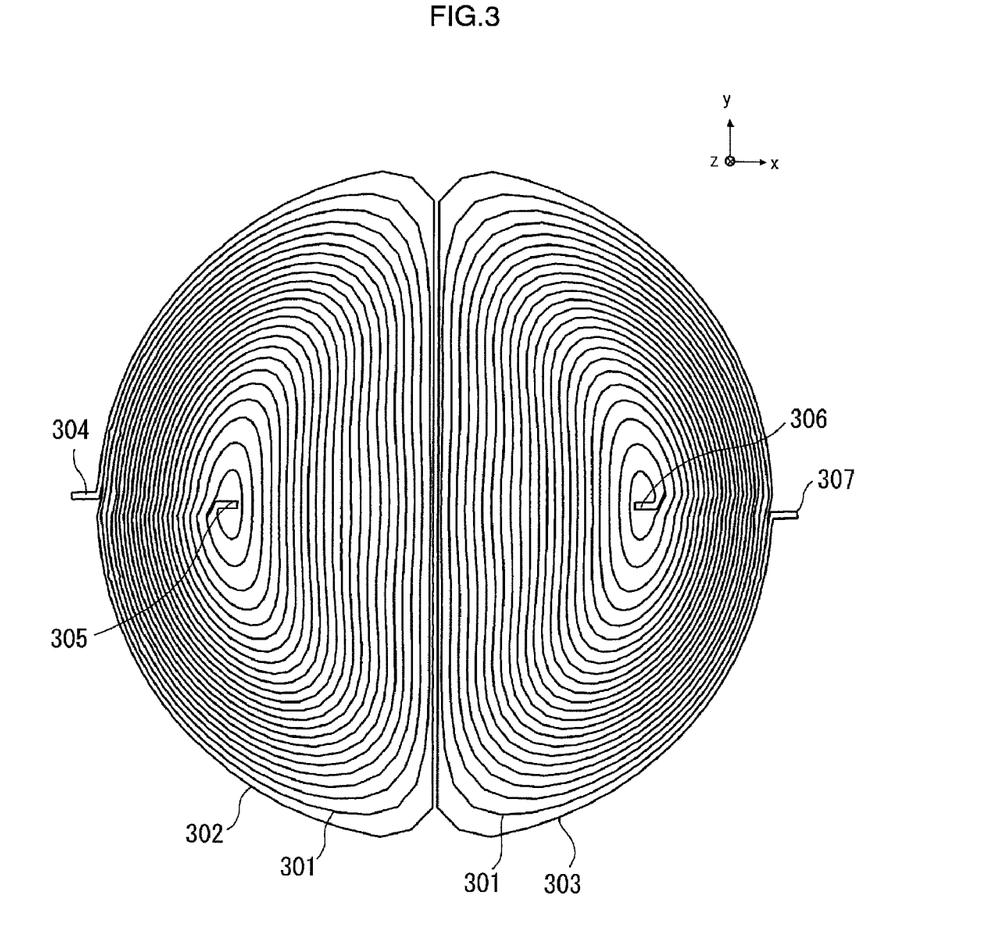
FIG. 3 is a diagram showing an x coil pattern of gradient magnetic field coils 108a, 108b of the MRI apparatus of FIG. 1.

For example, the x coil is configured so that two flat-plate type spiral coils each of which is formed by spirally cutting a slit 301 of 1 mm in width in a conductive plate (for example, copper plate) of 3 mm in thickness are arranged symmetrically at right and left sides (in the x-axis direction) as shown in FIG. 3, for example. Current is supplied from terminals 304, 305 and terminals 306, 307 so that the directions of magnetic fluxes generated by the left-side spiral coil 302 and the right-side spiral coil 303 are opposite to each other, thereby generating magnetic fluxes in directions of arrows 210 and 211 of FIG. 2 from the x coils of the upper and lower gradient magnetic field coils 108a and 108b.

These magnetic fluxes are convoluted with the magnetic flux generated by the superconductive magnet 101, whereby gradient magnetic field which gradually decreases in magnetic flux density is formed in the x-axis direction.

The y coil is constructed by rotating spiral coils 302 and 303 having the same pattern as the x coil by 90° and disposing them in the y-axis direction, thereby forming gradient magnetic field which gradually decreases in magnetic flux density in the y-axis direction.

Figure 4:
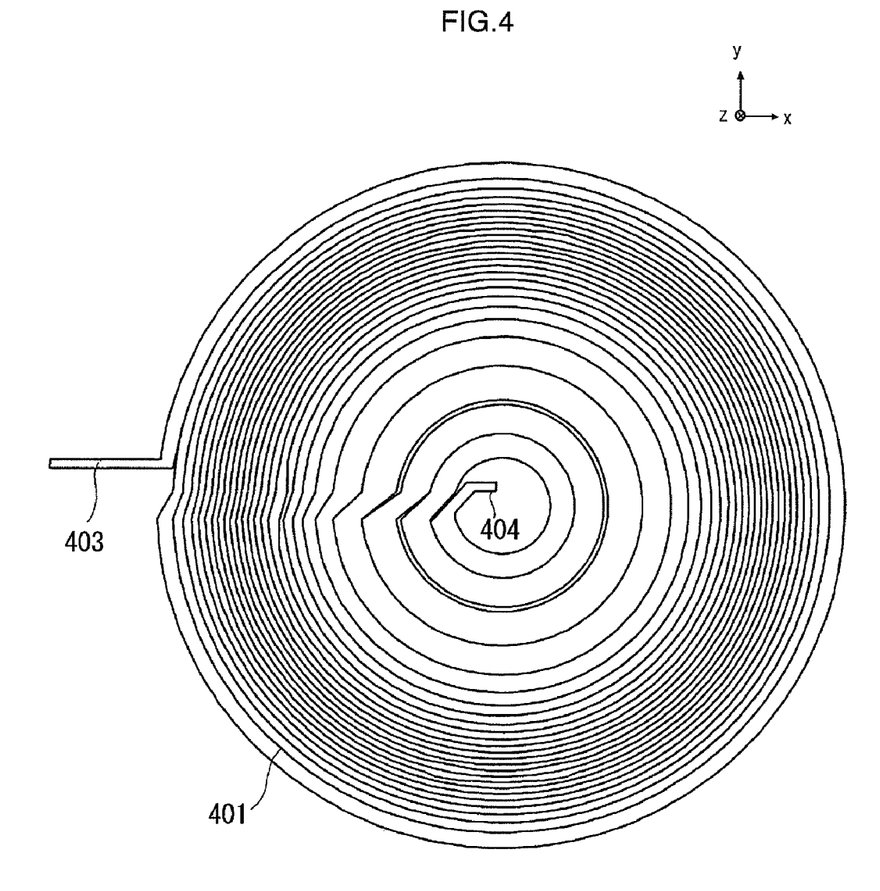
FIG. 4 is a diagram showing an z coil pattern of the gradient magnetic field coils 108a, 108b of the MRI apparatus of FIG. 1.

As shown in FIG. 4, the z coil is formed by spirally cutting a slit 401 of 1 mm in width in a conductive plate (for example, copper plate) of 3 mm in thickness, for example. Current is supplied from the terminals 403 and 404 of the z coil so that the z coil of the upper-side gradient magnetic field coil 108a generates a magnetic flux in the direction of an arrow 210 of FIG. 2, and the z coil of the lower-side gradient magnetic field coil 108b generates a magnetic flux in the direction of an arrow 211. Accordingly, a magnetic flux generated in the superconductive magnet 101 is convoluted with the magnetic fluxes of the upper and lower z coils, thereby forming gradient magnetic field which gradually decreases in magnetic flux density in the z-axis direction.

A gradient magnetic field power amplifier 109 is connected to each of the x coil, y coil and z coil of the gradient magnetic field coils 108a and 108b to independently supply current for only a desired time. In a general imaging pulse sequence, the operating frequency (switching frequency) of the gradient magnetic pulse is set to about several kHz to 10 kHz.

As shown in FIGS. 1 and 2, a shield supporter 110 is fixed to the vacuum container 207 at the imaging space 203 side of the upper cryostat 103 and the lower cryostat 104. As shown in perspective view and cross-sectional view of FIGS. 5(a), (b), the shield supporter 110 has a plate-like portion (disc plate) 110a parallel to the main flat planes of the upper and lower cryostats 103 and 104 and a leg portion 110b for supporting the upper and lower cryostats 103 and 104. The shield supporter 110 shown in FIGS. 5(a), (b) is configured so that the leg portion 110b is provided continuously over the peripheral edge portion of the plate-like portion 110a.

As shown in FIGS. 1 and 2, a high frequency shield 111 is secured to the inside of the plate-like portion 110a of the shield supporter 110 (the surface facing the gradient magnetic field coil 108a, 108b). Accordingly, the high frequency shield 111 is opposed to the gradient magnetic field coil 108a, 108b at a fixed interval (10 mm or more, in this case, at an interval of 10 mm, for example). The high frequency shield 111 is designed so as to shield the high frequency of the high frequency coil 112, pass the gradient magnetic field of the gradient magnetic field coil 108a, 108b therethrough and also reduce eddy current generated due to the passage of the gradient magnetic field. The detailed structure of the high frequency shield 111 will be described later.

Figure 5:
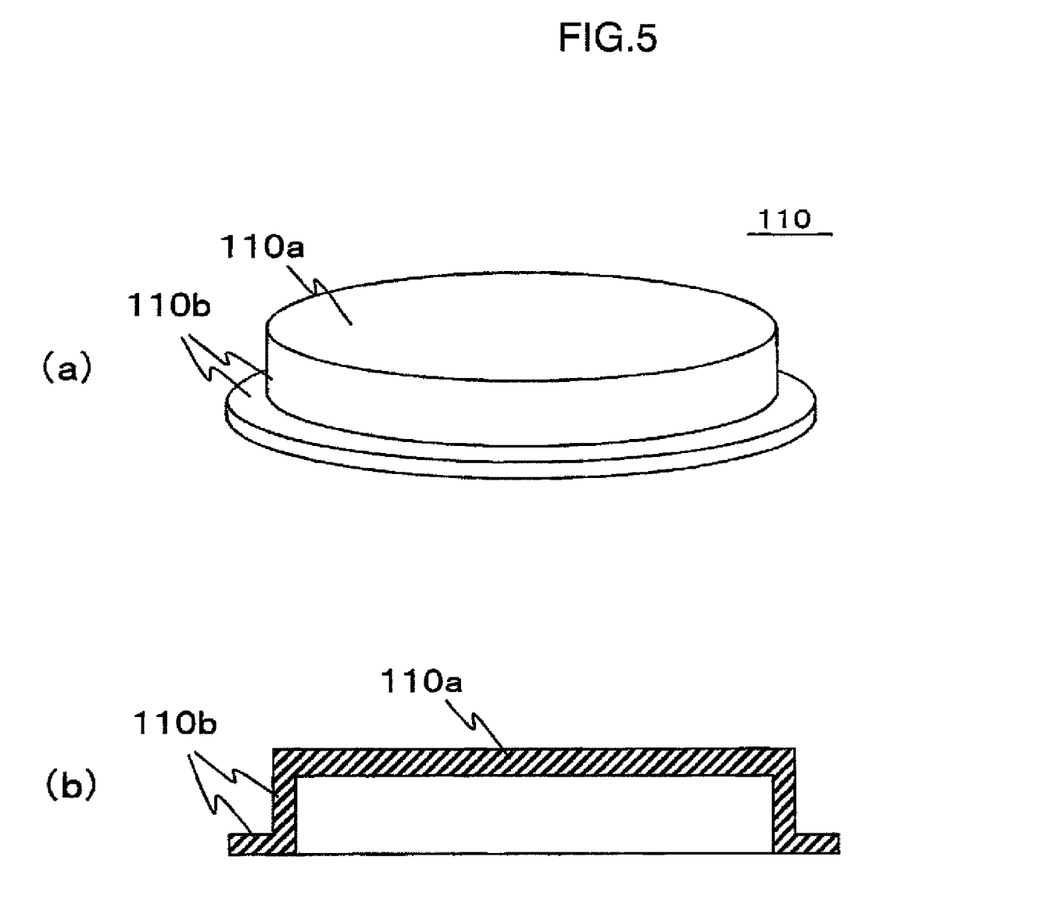

The plate-like portion 110a and the leg portion 110b of the shield supporter 110 is constructed by a firm plate-like member (for example, a fiber-reinforced plastic plate of 15 mm in thickness), whereby the rigidity of the shield supporter 110 is enhanced, and occurrence of vibration due to eddy current in the high frequency shield 111 is suppressed.

The shield supporter 110 is designed so as not to resonate at the operating frequency (the switching frequency of the gradient magnetic field pulse) of the gradient magnetic field coils 108a, 108b under the state that it supports the high frequency shield 111. Specifically, it is designed so that the natural frequencies of the high frequency shield 111 and the shield supporter 110 are different from the operation frequency of the gradient magnetic field coil.

Accordingly, even when vibration caused by eddy current occurs in the high frequency shield 111, the shield supporter 110 supporting the high frequency shield ill does not resonate, and thus the vibration of the high frequency shield 111 can be suppressed.

The natural frequency of the shield supporter 110 can be designed by using the shape based on the diameter, height, thickness, etc., the density of the material, etc. of the shield supporter 110 as parameters. Furthermore, in this embodiment, the shield supporter 110 having the shape shown in FIGS. 5(a), (b) is used. However, the natural frequency can be also controlled by providing a projection having a predetermined shape or an opening to the plate-like portion 110a or the leg portion 110b.

The shield supporter 110 is constructed so as to cover and hermetically seal the space in which the gradient magnetic field coils 108a and 108b are disposed, and thus it has an effect of suppressing aerial vibration emitted from the vibration of the gradient magnetic field coils 108a, 108b.

As shown in FIGS. 1 and 2, the high frequency coil 112 is mounted on the surface of the shield support member 110 (the surface at the imaging space 203 side). A coil having a flat-plate structure is also adopted as this high frequency coil 112 so as not to obstruct the open structure of the superconductive magnet 101. A well known coil pattern may be adopted as the coil pattern of the high frequency coil 112. The high frequency power amplifier 113 is connected to the pair of upper and lower high frequency coils 112 as shown in FIG. 1. High frequency current corresponding to the resonance frequency of nuclear spins (atomic nuclear spins of hydrogen) is made to flow by the high-frequency power amplifier 113, whereby high-frequency magnetic field which resonantly excites the nuclear spins can be applied to the examinee 102 in the imaging space 203. In the case of this embodiment, for example, 50 MHz which induces nuclear magnetic resonance to hydrogen atom at a magnetic field intensity of 1.2 tesla is selected.

A detection coil 114 for detecting an NMR signal is fixed to a position nearest to the examinee 102. The detection coil 114 receives an NMR signal emitted due to resonance of nuclear spins of the examinee 102, and converts it to an electrical signal. A high frequency amplifying circuit 115 is connected to the detection coil 114. The high frequency amplifying circuit 115 amplifies the NMR signal converted to the electrical signal, converts it to a digital signal and then delivers the digital signal to the computer 116.

A computer 116 reconstructs an image to be supplied for diagnosis from the NMR signal which has been converted to the digital signal. The reconstructed image is saved in a built-in memory device, and also displayed on a display 117.

A pulse sequencer (not shown) in the computer 116 feeds a control signal to the compressor unit 107, the gradient magnetic field power amplifier 109, the high frequency power amplifier 113 and the high frequency amplifying circuit 115 through a system signal bus line 118 to control the operation.

Here, the structure and action of the high frequency shield 111 will be described.

The frequency of the high frequency magnetic field generated by the high frequency coil 111 is equal to 50 MHz when the magnetostatic field intensity generated by the superconductive magnet 101 is equal to 1.2 tesla. The frequency of 50 MHz is far away from the audio frequency band. This frequency is too high for mechanical vibration of material constituting the shield supporter 110 or the high frequency coil 112. Therefore, it is unnecessary to pay attention to direct noise or vibration caused by high frequency magnetic field. However, the high frequency coil 112 is close to the gradient magnetic field coils 108a and 108b. Therefore, the electromagnetic interaction therebetween generates inductive inductance and floating capacity in the circuit of the high frequency coil 112 and thus adversely affects the circuit characteristic of the high frequency coil 112. Therefore, it is necessary that the high frequency shield 111 is disposed between the high frequency coil 112 and the gradient magnetic field coil 108a, 108b to shield the high frequency magnetic field (50 MHz) generated by the high frequency coil 112, and occurrence of inductive inductance or floating capacitance in the high frequency coil 112 is prevented.

It is ideal as the characteristic of the high frequency shield 111 to substantially perfectly shield the high frequency magnetic field of 50 MHz generated by the high frequency coil 112 and pass the gradient magnetic field generated by the gradient magnetic field coils 108a, 108b therethrough with no influence. The action of shielding the high frequency magnetic field can be attained by forming the high frequency shield 111 of a thin and uniform conductor, for example, a conductive foil. However, when the high frequency shield 111 is constructed by a uniform conductor, eddy current is generated by a gradient magnetic field pulse which is switched at a frequency of several kHz to 10 kHz, and it affects the waveform of the gradient magnetic field pulse. Furthermore, vibration caused by eddy current occurs in the high frequency shield 111. In order to reduce eddy current, it is considered to divide the conductive foil of the high frequency shield. However, it does not function as a uniform conductor, and the high frequency magnetic field shielding characteristic of the high frequency shield is deteriorated.

Therefore, according to this embodiment, the high frequency shield 111 is constructed so as to have low resistance to the high frequency magnetic field of 50 MHz as if it can be regarded as a substantially uniform conductor, and also have high resistance to alternate magnetic field from several kHz to 10 kHz corresponding to the operating frequency of the gradient magnetic field.

Specifically, as shown in top view of FIG. 6(a) and cross-sectional view of FIG. 6(b), the high frequency shield 111 is constructed so that two circular conductive foils 501 and 503 are attached to both the surfaces of a resin sheet 502, and the circular conductive foil 501, 503 is divided into 16 sectors having an equal center angle. That is, the circular conductive foil 501 is divided into sixteen sectoral conductive foils 501a to 501p, and the adjacent conductive foils do not come into direct contact with each other. Likewise, the circular conductive foil 503 is divided into 16 sectoral conductive foils 503a to 503p, and the adjacent sectoral conductive foils do not come into direct contact with each other. The dividing positions of the circular conductive foil 501 are displaced from the dividing positions of the circular conductive foil 503 by about 10°.

In this case, the thickness of the circular conductive foil 501, 503 is set to 15 μm, and the diameter thereof is set to 1 m. The conductive foil is desired to be non-magnetic and have low resistance, and for example, copper foil or aluminum foil is used. The resin sheet 502 is a dielectric member, and an epoxy resin sheet may be used, for example. In this case, the thickness of the resin sheet 502 is set from not less than 0.5 mm to not more than 1.0 mm.

The dividing positions of the circular conductive foil 501 are displaced from the dividing positions of the circular conductive foil 503 by about 10°. Therefore, as is apparent from FIG. 6(b), the sectoral conductive foil 501a is opposed to the sectoral conductive foil 503a and the sectoral conductive foil 503p through the resin sheet 502 as a dielectric member, thereby constituting a capacitance element (capacitor). The sectoral conductive foil 503a is opposed to the sectoral conductive foil 501a and the sectoral conductive foil 501b through the resin sheet 502, thereby constituting a capacitance element. That is, the sectoral conductive foils at both the surface sides of the resin sheet 502 constitute the capacitance element with the resin sheet 502 as the dielectric member, and the adjacent capacitance element and sectoral conductive foil are shared. Accordingly, as shown in an equivalent circuit of FIG. 6(c), all the capacitance elements constructed by the sectoral conductive foils are equivalent to a serially connected circuit.

The diameter of the high frequency shield 111 of this embodiment is set to about 1 m, and when the value of the capacitance element constructed by the sectoral conductive foil is experimentally determined, it is equal to about 2500 pF. This equivalent capacitance element (capacitor) has low resistance of $1.3\Omega = 1/(j\omega C)$ to high frequency magnetic field of 50 MHz generated by the high frequency coil 112. Accordingly, the high frequency shield 111 works as a perfectly circular copper sheet (uniform conductor) of 1 m in diameter in the high frequency magnetic field of the high frequency coil 112, and can substantially perfectly shield the high frequency magnetic field. Therefore, the interference between the gradient magnetic field coil and the high frequency coil can be prevented.

The resistance value of $1.3\Omega$ is a load which can be regarded as a substantially uniform conductor for the following reason. A coaxial cable having a characteristic impedance of $50\Omega$ is generally used for the connection between the high frequency coil 112 and the high frequency power amplifier 109. Therefore, the impedance of the high frequency coil 112 is also adjusted to $50\Omega$. If the load variation is within 5% of $50\Omega$, that is, the resistance value is not more than $2.5\Omega$, this apparatus can be sufficiently permitted as the MRI apparatus. This is because the loss of the dielectric member due to insertion of an object being examined varies the characteristic impedance of the high frequency coil 112 by 10% to 20%. Accordingly, it can be regarded that the high frequency shield having the resistance value of $1.3\Omega$ can substantially shield the high frequency magnetic field of the high frequency coil 112.

Figure 7:
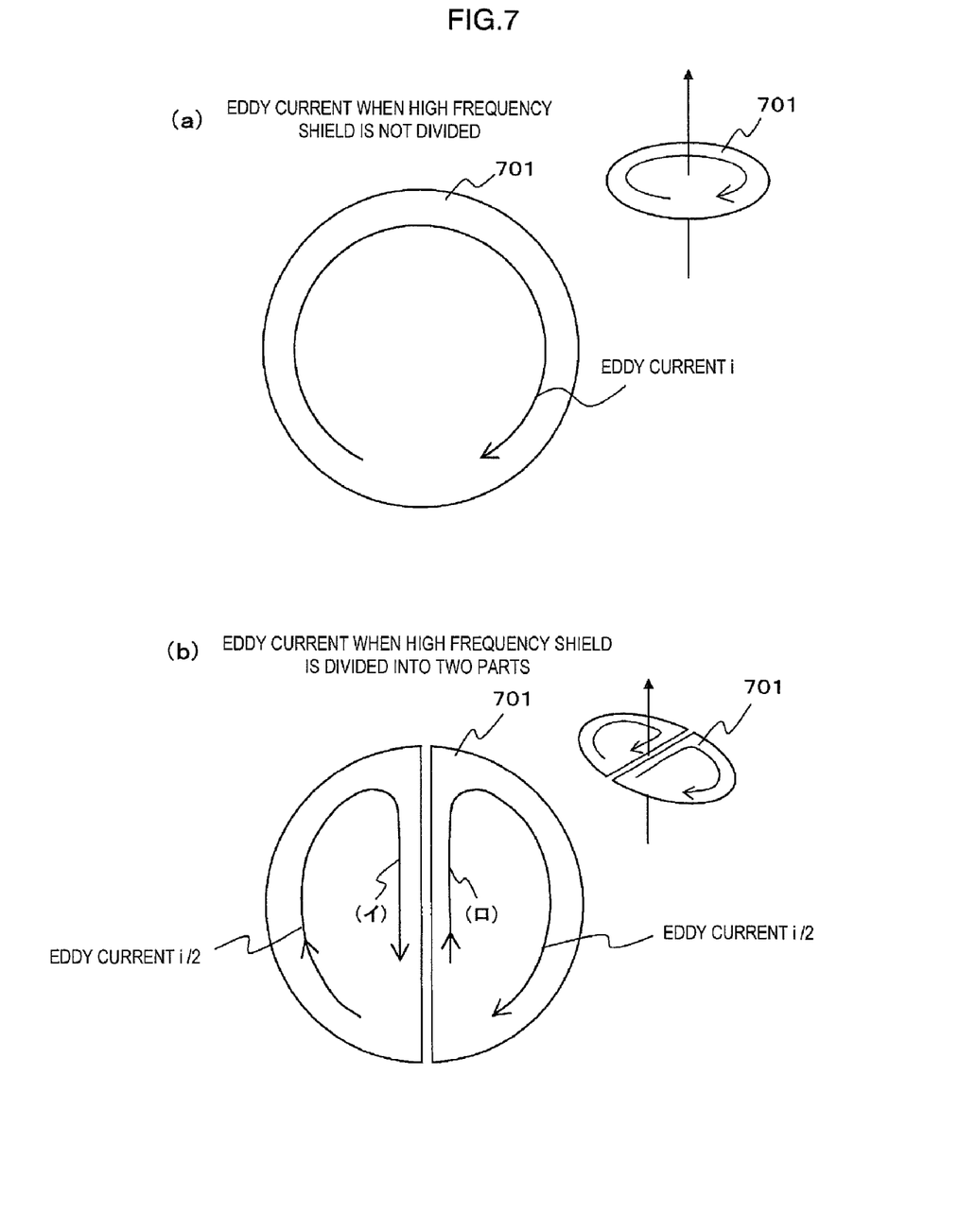

The equivalent capacitance element constituting the sectoral conductive foil has high resistance of $50\,k\Omega$ to alternate magnetic field of several kHz to 10 kHz generated by the gradient magnetic field coil 108. Occurrence of eddy current is caused by the sixteen divided sectoral conductive foils, however, the current value of the eddy current is reduced. This will be described with reference to FIGS. 7(a), (b). When gradient magnetic field passes through a non-divided uniform circular conductive foil 701 as shown in FIG. 7(a) and thus eddy current flows, the eddy current value i is induced by a magnetic flux $\Phi$ traversing the overall area of the conductor. Next, by dividing the circular conductive foil into two parts as shown in FIG. 7(b), the magnetic flux $\Phi'$ traversing the conductive foil having a half area is equal to ½. The switching rate of the gradient magnetic field is unvaried, and thus the eddy current value i' flowing through the conductive foil having the half area is equal to i/2. At the boundary portion between the divided parts, the direction (a) of the eddy current flowing through the conductive foil is opposite to the direction (b) of the eddy current flowing through the other conductive foil, and also the current density is equal therebetween, so that they are offset with each other. Accordingly, the eddy current is equivalent to eddy current of i/2 as the overall circular conductive foil.

Figure 6:
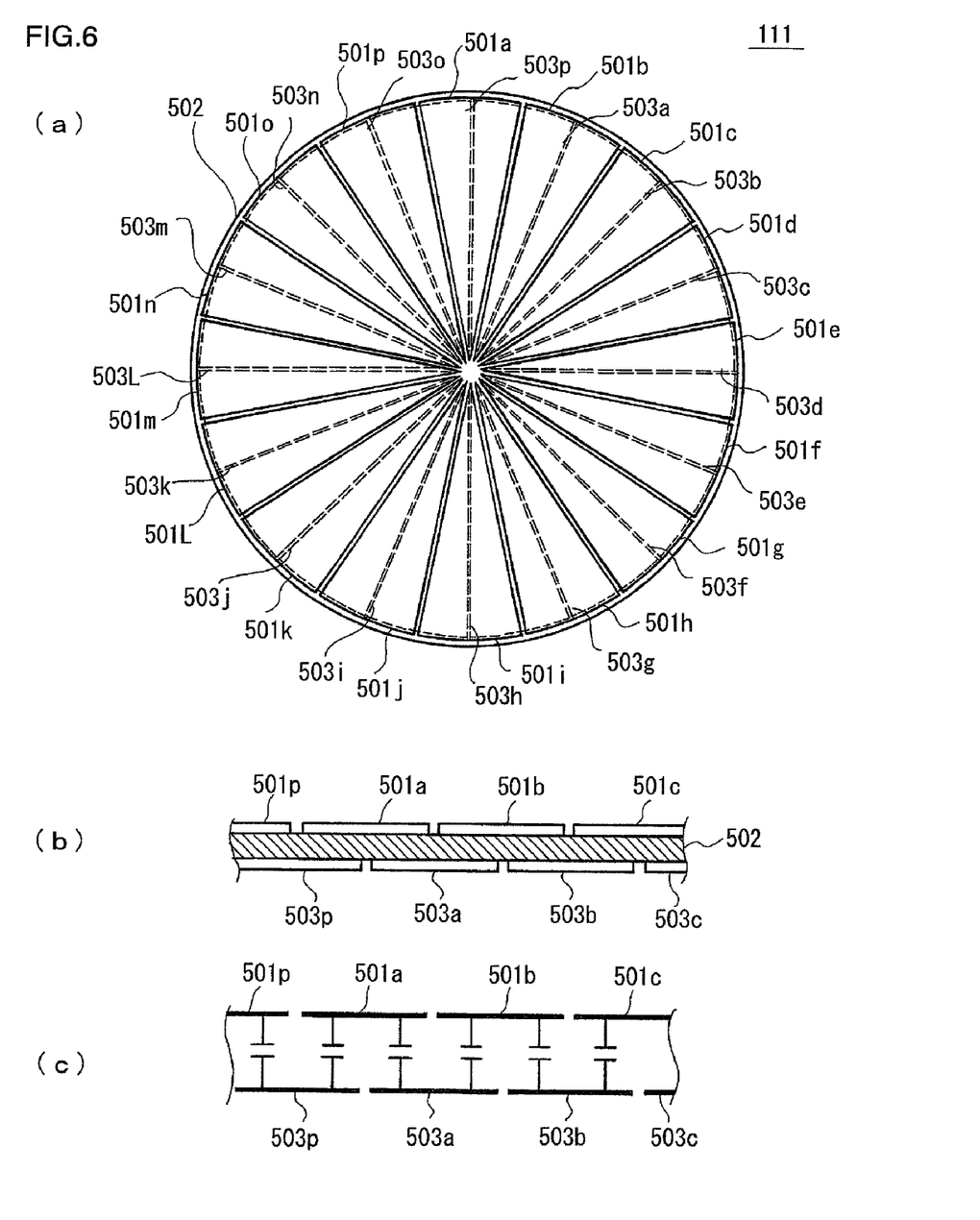

Accordingly, it is apparent that eddy current is reduced in proportion to the dividing number of the conductive foil. The high frequency shield 111 of FIG. 6(*a*) is obtained by dividing the circular conductive foil 501, 503 into sixteen parts, and thus the magnitude of eddy current can be reduced to 1/16 as compared with the case where the circular conductive foil 501, 503 is not divided.

As described above, the high frequency shield 111 of this embodiment has the characteristic that eddy current based on gradient magnetic field can be greatly reduced with keeping the characteristic of shielding the high frequency magnetic field of the high frequency coil 112.

Here, there will be described the operation of each of parts when a high-speed imaging method for switching strong gradient magnetic field represented by echo planar imaging (EPI) is carried out by using the MRI apparatus of this embodiment. The pulse sequence in the computer 116 transmits a control signal to each of the compressor unit 107, the gradient magnetic field power amplifier 109, the high frequency power amplifier 113 and the high frequency amplifying circuit 115 at a predetermined timing to execute a predetermined imaging pulse sequence. That is, high frequency magnetic field (frequency of 50 MHz) is applied from the high frequency coil 112 to the examinee 102 at a predetermining timing, and a strong gradient magnetic field pulse is applied from the gradient magnetic field coils 108*a*, 108*b* at a frequency of several kHz to 10 kHz while switched at high speed. An NMR signal generated from the examinee 102 is received by the detection coil 114, and an image is re-constructed by the computer 116.

At this time, the high frequency shield 111 has low resistance to the high frequency magnetic field (frequency of 50 MHz) in the direction from the high frequency coil 112 to the gradient magnetic field coils 108*a*, 108*b*, so that it can act as an uniform conductive foil and shield this. Accordingly, the high frequency coil 112 is electromagnetically shielded to the gradient magnetic field coils 108*a* and 108*b*, and the operation of the high frequency coil 112 can be prevented from being unstable due to the inductive inductance or the floating capacitor.

On the other hand, the strong gradient magnetic field pulse (several KHz to 10 kHz) from the gradient magnetic field coils 108*a* and 108*b* pass through the high frequency shield 111. However, the circular conductive foil 501, 503 of the high frequency shield 111 is divided into 16 parts, and thus the eddy current thereof is reduced to about 1/16 as compared with the case where the non-divided circular conductive foil is used. Accordingly, a magnetic flux generated by the eddy current is coincident with the direction of the magnetostatic field, however, the eddy current value is small, so that the strength of vibration caused by the electromagnetic force action is also weak.

The high frequency shield 111 is fixed to the shield supporter 110 having large rigidity. Therefore, even when weak vibration occurs in the high frequency shield 111, the shield supporter 111 having large rigidity suppresses vibration of the high frequency shield 111. Furthermore, the natural frequency of the shield supporter 110 is designed to be different from the switching frequency (several kHz to 10 kHz) of the gradient magnetic field. Therefore, it resonates with the vibration of the high frequency shield 111, and thus large vibration does not occur.

Accordingly, the MRI apparatus of this embodiment has an open structure, however, even when large gradient magnetic field is switched at high speed, the vibration of the high frequency shield can be suppressed and thus the high frequency shield can be prevented from serving as a noise source. According to inventors' experiments, as compared with the case where circular conductive foil is used as the high frequency shield, the MRI apparatus of this embodiment can improve the vibration noise by 5 dB.

In addition, the high frequency magnetic field shielding capability of the high frequency shield 111 is kept. Therefore, none of inductance and floating capacitance occur uniform high frequency magnetic field can be applied to the examinee 102. Furthermore, eddy current occurring when the gradient magnetic field pulse passes through the high frequency shield 111 is small, and thus there is obtained an effect that the influence of the high frequency shield 111 on the gradient magnetic field pulse is small. There has hitherto occurred a problem that blunting of the switching speed of the gradient magnetic field pulse and reduction of the intensity amplitude of the gradient magnetic field pulse are caused by occurrence of eddy current when a gradient magnetic field pulse passes through the high frequency shield, and this causes an error of a position encode, so that the spatial resolution of the MRI image is deteriorated. However, according to this embodiment, the blunting of the switching speed of the gradient magnetic field pulse and the reduction of the intensity amplitude of the gradient magnetic field pulse do not occur, so that a high-precision image can be picked up with high spatial resolution.

Furthermore, according to this embodiment, eddy current generated in the high frequency shield 111 is small, and thus the heat amount is also small, so that there is obtained an effect of preventing the temperature increase of the imaging space. There has hitherto occurred a problem that eddy current is consumed as heat by the conductor resistance of the high frequency shield and thus the high frequency shield is heated. The conventional high frequency shield shields the high frequency magnetic field of 50 MHz by a skin effect, and thus it is generally constructed by a thin copper foil of about 20 μm to 50 μm. Therefore, the high frequency shield has properties such as large conductor resistance and small heat capacity, and thus there occurs a problem that the high frequency shield is heated in a continuous examination. For example, it may be heated up to 100° C. or more in a continuous examination of about 30 minutes, and thus the temperature of the mount space of the examinee is increased. However, in this embodiment, the high frequency magnetic field shielding capability of the high frequency shield 111 is kept and occurring eddy current is small, so that the temperature increase of the mount space of the examinee can be prevented.

Furthermore, the high frequency shield 111 is supported by the shield supporter 110 having large rigidity. Therefore, a gap exists between the gradient magnetic field coil 108*a*, 108*b* and the high frequency shield 111, and thus the position of the high frequency shield 111 is not varied even when thermal expansion and contraction occurs in the gradient magnetic field coils 08*a* and 108*b*. Accordingly, the mutual position between the high frequency coil 112 and the high frequency shield 111 is fixed, and the stable high frequency magnetic field can be supplied in the imaging space 203.

The shield supporter 110 hermetically seal the space in which the gradient magnetic field coils 108a and 108b are disposed, so that the vibration sound of the gradient magnetic field coils can be shielded.

Furthermore, the resonance frequency of the gradient magnetic field coils 108a and 108b can be deviated from the frequency band of the imaging sequence by the rubber cushion 208, and also the vibration energy of the gradient magnetic field coils 108 can be attenuated.

Figure 8:
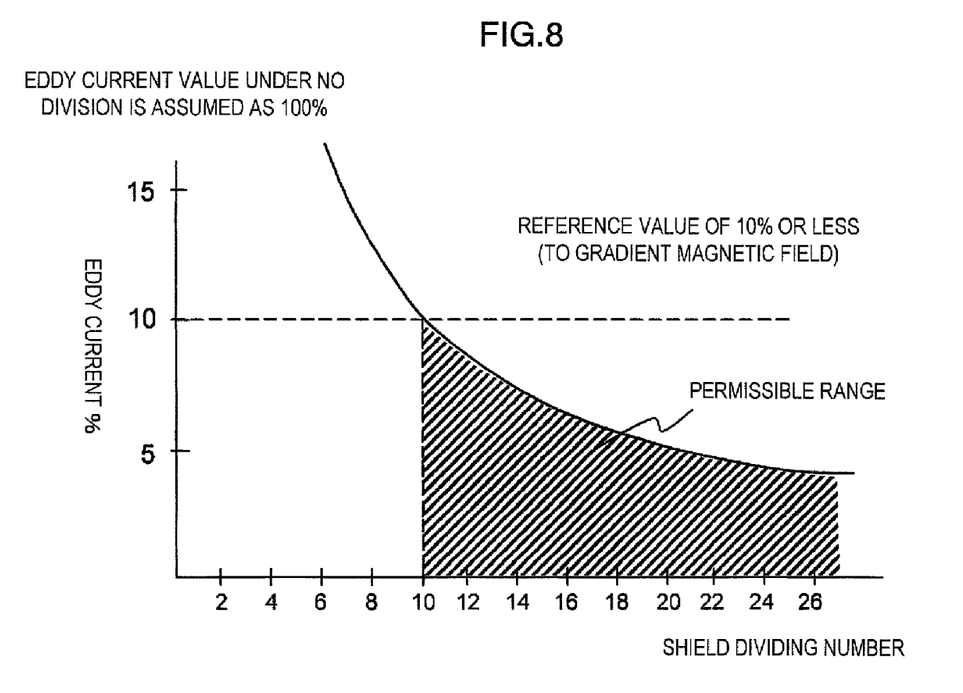
FIG. 8 is a graph showing the relation between the dividing number of the high frequency shield 111 and the magnitude of the eddy current.

In the above embodiment, each of the circular conductive foils 501 and 503 of the high frequency shield 111 is divided into sixteen parts, however, the present invention is not limited to this embodiment. As described above, the magnitude of the eddy current occurring in the circular conductive foils 501, 503 is reduced in inverse proportion to the dividing number. Accordingly, when the eddy current value in the case of the non-divided circular conductive foil is assumed to be 100%, the relation between the dividing number and the eddy current value is shown in FIG. 8. Accordingly, the lower limit of the dividing number can be selected on the basis of the permitted magnitude of the eddy current. For example, when it is necessary to set the magnitude of eddy current to ¹/₁₀ (that is, 10%) as compared with the non-division case, the dividing number of the circular conductive foils 501, 503 of the high frequency shield 111 is set to ten or more.

Figure 9:
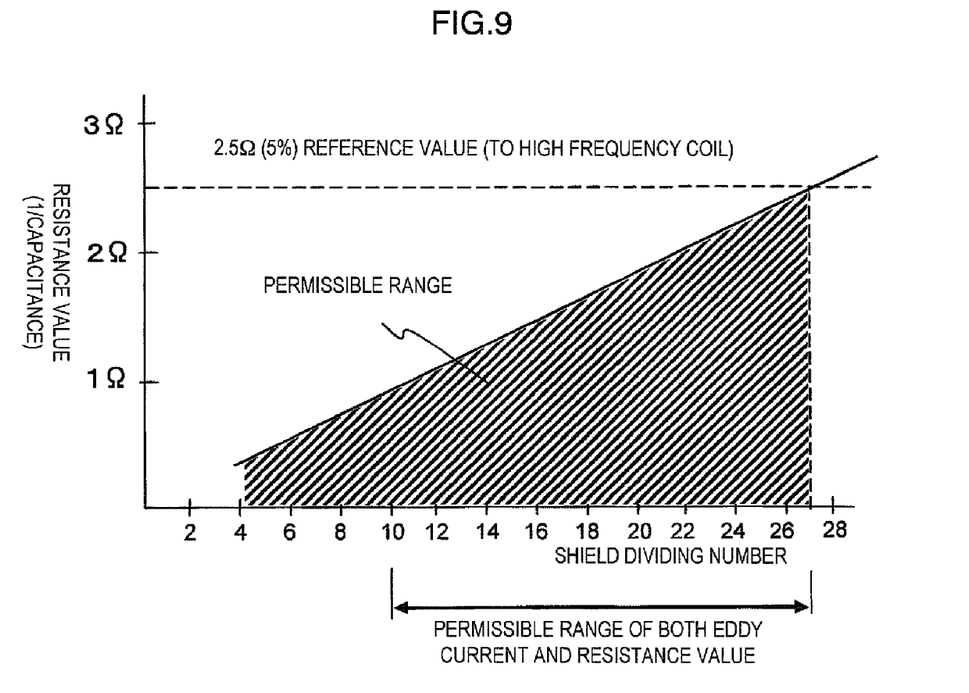
FIG. 9 is a graph showing the relation between the dividing number of the high-frequency shield 111 and the resistance value to high frequency magnetic field.

On the other hand, when the dividing number of the circular conductive foils 501, 503 of the high frequency shield 111 increases, the area of the sectoral conductive foil decreases in inverse proportion to the dividing number, and the capacitance (C) of the capacitance element decrease. Accordingly, as shown in FIG. 9, the resistance value to the high frequency magnetic field (50 MHz) of the high frequency shield 111 increases in proportion to the dividing number. With respect to the resistance value to the high frequency magnetic field (50 MHz), the permissible range thereof is within about 5% of the impedance of the high frequency coil 112 as described above, and thus the upper limit of the dividing number is set so that the resistance value concerned satisfies the permissible range. For example, when the impedance of the high frequency coil 112 is equal to 50Ω, the dividing number is set to 27 or less so that 2.5Ω is attained as the permissible value of the resistance value.

Accordingly, when the eddy current is set to 10% or less of the non-division case, that is, when the impedance of the high frequency coil is equal to 50Ω, the dividing number of the high frequency shield 111 is desired to be set to a value from not less than 10 to not more than 27.

(Second Embodiment)

Next, an MRI apparatus according to a second embodiment will be described.

Figure 10:
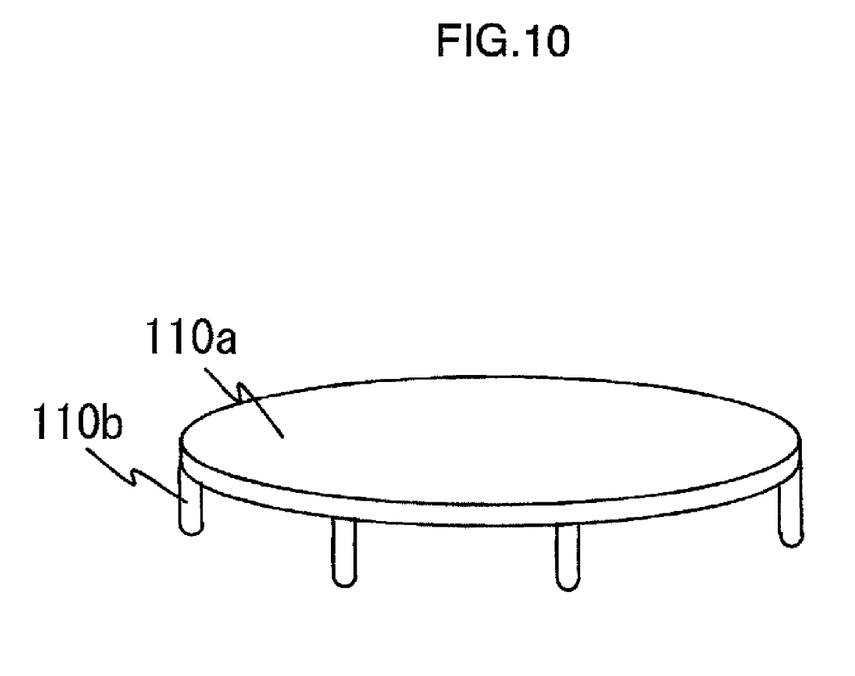
FIG. 10 is a perspective view showing a shield support member according to a second embodiment.

In the second embodiment, a shield supporter having a shape shown in FIG. 10 is used as the shield supporter 110. The shield supporter 110 of FIG. 10 is configured to have plural cylindrical leg portions 110b on a disc-shaped plate-like portion 110a. The high frequency shield 111 is supported on the inner surface of the plate-like portion 110a as in the case of FIGS. 1 and 2, and the high frequency coil 112 is supported on the outer surface. The structures of the high frequency shield 111, etc. excluding the shield supporter 110 are the same as the first embodiment, and thus the description thereof is omitted. The shield supporter 110 has sufficient rigidity to support the high frequency shield 111, and also the shape and the thickness and arrangement of the leg portions 110b are designed so that the natural vibration thereof under the state that it supports the high frequency shield 111 is different from the operating (switching) frequency of the gradient magnetic field coils 108a, 108b.

With respect to the shield supporter 110 having the shape shown in FIG. 10, it is impossible that the gradient magnetic field coil 108a, 108b is disposed to hermetically seal the space as in the case of the shield member 110 of FIGS. 5(a), (b) of the first embodiment. However, it can support the high frequency shield 111 with sufficient strength, and the rigidity of the high frequency shield 111 can be enhanced. Accordingly, even when eddy current occurs in the high frequency shield 111 and thus vibration caused by the eddy current occurs, the vibration can be suppressed. Furthermore, the natural frequency of the shield supporter 110 is deviated from the switching frequency of the gradient magnetic field, so that the high frequency shield 111 does not resonate with the switching of the gradient magnetic field and thus vibration can be prevented.

The resonance frequency of the shield supporter 110 can be controlled by providing a rod-shaped projection or an opening to the plate-like portion 110a. Furthermore, the resonance frequency can be controlled by varying the number or arrangement of the leg portions 110b or irregularly arranging the leg portions 110b.

(Third Embodiment)

Figure 11:
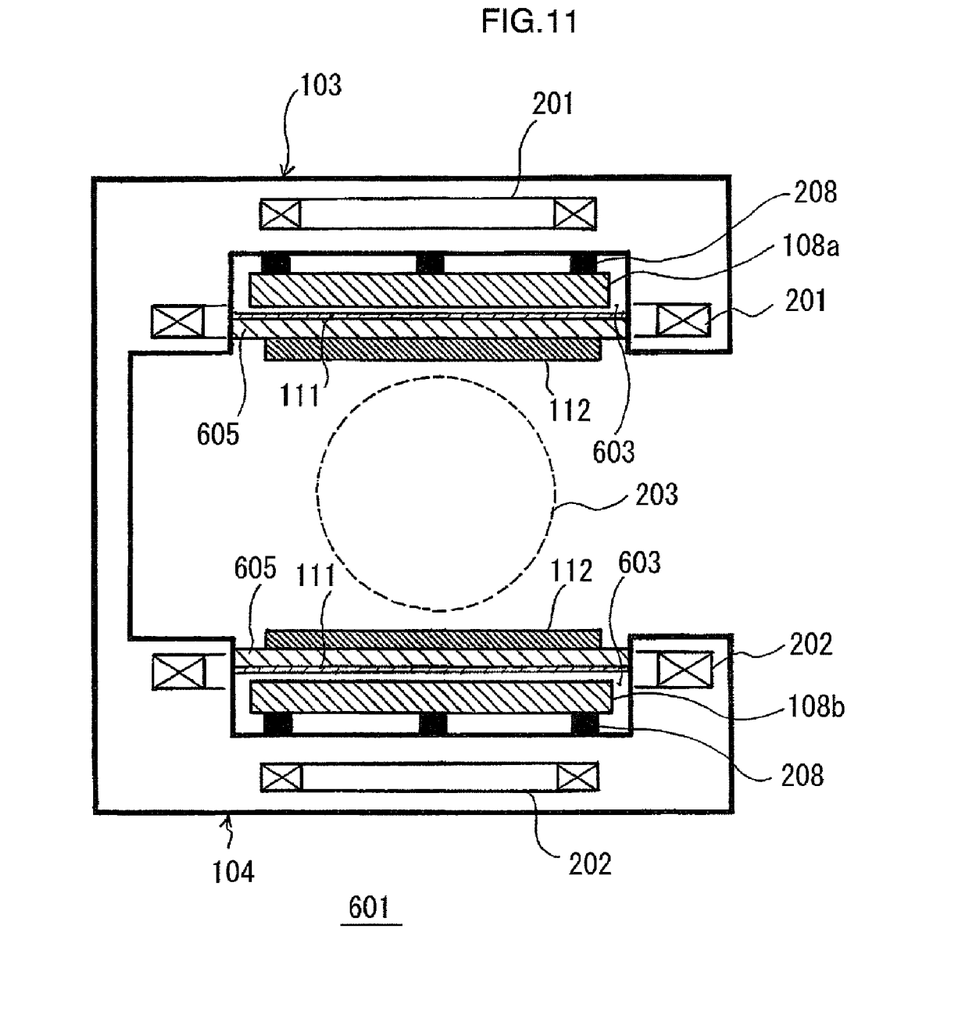
FIG. 11 is a cross-sectional view showing the structure of a superconductive magnet 601 of an MRI apparatus according to a third embodiment.

An MRI apparatus according to a third embodiment of the present invention will be described in FIG. 11. As shown in FIG. 11, the MRI apparatus of the third embodiment uses a superconductive magnet 601 having recess portions 603 which are provided to the surfaces at the imaging space side of the upper cryostat 103 and the lower cryostat 104.

The superconductive magnet of the MRI apparatus is generally desired to increase the magnetostatic field intensity of the imaging space while reducing the magnetomotive force of the superconductive coil, enhance the stability of the superconductive coil and reduce the manufacturing cost. Particularly, these are important elements for the superconductive magnet having the open structure. These elements can be easily implemented by reducing the interval between the upper cryostat 103 and the lower cryostat 104 which are opposed to each other. If the interval is reduced, it contradicts the purpose of the open MRI apparatus that the mount space of the examinee is required to be as broad as possible. Therefore, according to the third embodiment, as a countermeasure to this contradictory purpose, the vacuum container and the helium container of the upper and lower cryostats 103, 104 are provided with recess portions 603, and the gradient magnetic field coils 108a, 108b are accommodated in the recess portions 603.

The recess portions 603 are shaped in conformity with the shapes of the superconductive coil 201, 202 accommodated in the upper and lower cryostats 103 and 104 so as not to obstruct the superconductive coils 201 and 202. In FIG. 11, each of the superconductive coils 201 and 202 comprises two coils, and one of the coils (main coil) is disposed at the outer peripheral portion of the recess portion 603. The gradient magnetic field coil 108a, 108b is fixed to the vacuum container of the bottom surface of the recess portion 603 through plural rubber cushions 208. Accordingly, the mount space of the examinee (the imaging space 203 and the surrounding space thereof) can be broadened by only the thickness of the gradient magnetic field coil 108a while the interval between the superconductive coil 201 and the superconductive coil 202 is kept in the same level as the apparatus shown in FIGS. 1 and 2.

The shield supporter 605 is fixed to the opening of the recess portion 603 so as to be spaced from the gradient magnetic field coil 108a, 108b at an interval of 10 mm. The shield supporter 605 is formed of a plate-like FRP (fiber reinforced plastic) of 20 mm in thickness. The peripheral edge portion of the shield supporter 605 is firmly fixed to the wall surface of the recess portion 603 by plural bolts (not shown), whereby the rigidity of the shield supporter 605 is enhanced. The high frequency shield 111 is attached to the face of the shield supporter 605 which faces the gradient magnetic field coil 108, and the high frequency coil 112 is secured to the surface of the shield supporter 605.

The shield supporter 605 has sufficient rigidity to support the high frequency shield 111, and also the thickness, the material, the fixing positions of the bolts, etc. are designed so that the natural frequency under the state that the high frequency shield 111 is supported is different from the operating (switching) frequency of the gradient magnetic field coil 108*a*, 108*b*.

The other constructions of the high frequency shield 111, etc. are the same as the first embodiment, and thus the description thereof is omitted.

The shield supporter 605 having the shape shown in FIG. 11 can support the high frequency shield 111 with sufficient strength, and the rigidity of the high frequency shield 111 can be enhanced. Accordingly, even when weak eddy current occurs in the high frequency shield 111 and vibration caused by the eddy current occurs, the vibration can be suppressed. Furthermore, since the natural frequency of the shield supporter 605 is deviated form the switching frequency of the gradient magnetic field, the high frequency shield 111 does not resonate with the switching of the gradient magnetic field, and thus the vibration can be prevented.

An O ring (not shown) is disposed in the gap between the surrounding end face of the shield supporter 605 and the wall surface of the recess portion 603, whereby the airtightness of the spaces in which the gradient magnetic field coils 108*a* and 108*b* are disposed can be enhanced, and noise emitted from the gradient magnetic coils 108 can be shielded.

The invention claimed is:

1. An open type magnetic resonance imaging apparatus comprising: a pair of magnetostatic field generators that are divisionally arranged at upper and lower sides of an imaging space in which an examinee is placed; a pair of gradient magnetic field generators that are disposed at the imaging space sides of the pair of magnetostatic field generators; and a pair of high frequency generators that are disposed at the imaging space sides of the gradient magnetic field generators, wherein a high frequency shield is disposed between each gradient magnetic field generator and each high frequency generator to shield electromagnetic field generated by the high frequency generator, and the high frequency shield has a structure of suppressing vibration occurring in the high frequency shield due to switching of gradient magnetic field generated by the gradient magnetic field generator.

2. The open type magnetic resonance imaging apparatus according to claim 1, wherein the high frequency shields are fixed to support members fixed to the surfaces of the imaging space sides of the pair of magnetostatic field generators as the structure of suppressing the vibration.

3. The open type magnetic resonance imaging apparatus according to claim 2, wherein the natural frequency of the support member is set to a frequency different from a switching frequency of the gradient magnetic field of the gradient magnetic field generator under the state that the high frequency shield is fixed to the support member.

4. The open type magnetic resonance imaging apparatus according to claim 1, wherein with respect to the high frequency shield, electric resistivity thereof to high frequency magnetic field generated by the high frequency generator is lower than electric resistivity to a switching frequency of gradient magnetic field generated by the gradient magnetic field generator.

5. The open type magnetic resonance imaging apparatus according to claim 1, wherein the high frequency shield contains two conductive sheets and a dielectric sheet sandwiched therebetween, and the two conductive sheets are respectively divided into plural parts at different positions.

6. The open type magnetic resonance imaging apparatus according to claim 5, wherein the high frequency shield constitutes serially connected capacitance elements by plural divided conductive sheets and a dielectric sheet sandwiched therebetween.

7. The open type magnetic resonance imaging apparatus according to claim 5, wherein the two conductive sheets are divided into parts whose number ranges from not less than 10 to not more than 27.

8. The open type magnetic resonance imaging apparatus according to claim 2, wherein the support member supports the high frequency shield at a position which is spaced from the gradient magnetic field generator at a predetermined interval.

9. The open type magnetic resonance imaging apparatus according to claim 2, wherein the support member also serves as a shielding member that covers the gradient magnetic field generator on the imaging space side of the magnetostatic field generator so that a space in which the gradient magnetic field generator is disposed is made a closed space.

10. The open type magnetic resonance imaging apparatus according to claim 2, wherein the magnetostatic field generator has a recess portion on the surface thereof at the imaging space side, the gradient magnetic field generator is disposed in the recess portion and the support member shields an opening of the recess portion.

11. The open type magnetic resonance imaging apparatus according to claim 2, wherein the support member has a flat portion parallel to the magnetostatic field generator and a leg portion for supporting the flat portion on the magneto static field generator.

12. The open type magnetic resonance imaging apparatus according to claim 2, wherein the support member is configured to have plural cylindrical leg portions on a disc-shaped plate-like portion.

13. The open type magnetic resonance imaging apparatus according to claim 2, wherein the support member is formed of fiber reinforced plastic.

14. The open type magnetic resonance imaging apparatus according to claim 8, wherein the predetermined interval is set to 10 cm or more.

15. The open type magnetic resonance imaging apparatus according to claim 5, wherein the dividing positions of the two conductive sheets are displaced from one another.

* * * * *